United States Patent [19]

Vaddadi

[11] Patent Number: 5,837,731
[45] Date of Patent: Nov. 17, 1998

[54] FATTY ACID TREATMENT

[75] Inventor: Krishna S Vaddadi, Clayton, Australia

[73] Assignee: Scotia Holdings Plc, United Kingdom

[21] Appl. No.: 721,329

[22] Filed: Sep. 26, 1996

[30] Foreign Application Priority Data

Sep. 27, 1995 [GB] United Kingdom ............... 9519661

[51] Int. Cl.$^6$ ................................................. A61K 31/20
[52] U.S. Cl. ............................................................ 514/560
[58] Field of Search .............................................. 514/560

[56] References Cited

PUBLICATIONS

WPIDS Abstract AN 95–036098, Kyle et al, corresponding to WO 9428913, Dec. 22, 1994.

Prostaglandins, Leukotrienes and Essential 1–3 Fatty Acids (U.K.) vol. 55, No. 1–2, 1996 pp. 89–94 Vaddadi "Dyskinesias and their treatment with essential fatty acids: a review".

WPIDS Abstract AN 94–067565 (Mosh et al), corresponds to EPA 0,585,087, Mar. 2, 1994.

Chemical Abstracts AN 1988:629345, Manku et al. Jan. 1988.

*Primary Examiner*—Keith D. MacMillan
*Attorney, Agent, or Firm*—Nixon & Vanderhye

[57] ABSTRACT

A method of treating Huntington's Chorea by the administration of effective amounts of GLA or DGLA and a method of delaying the onset of Huntington's Chorea or preventing it altogether by administering appropriate amounts of GLA or DGLA to clinically normal individuals who are genetic carriers of the disease, and a method of preparation of medications for such purpose using such acids.

4 Claims, No Drawings

FATTY ACID TREATMENT

FIELD OF INVENTION

The invention relates to treatment of Huntington's Chorea (HC).

BACKGROUND

HC is a disastrous neurological disease which effects 5–10 per 100,000 people in the Western world. It is an inherited disease with an autosomal dominant pattern of inheritance. This means that the children of parents of either sex with HC have a 50% chance of inheriting the gene. The gene invariably produces its effects (100% penetrance) but the age of onset varies considerably. It may develop in early childhood or not become manifest until after the age of 70. In most individuals the symptoms begin between the ages of 30 to 50. Individuals who inherit the disease from their father often have a considerably earlier age of onset than do those who inherit the disease from their mother. This variability depending on maternal or paternal inheritance and on unknown lifestyle events indicates that the expression of the HC gene is susceptible to at least some modulation.

HC is characterised by a particular type of movement disorder, particularly characterised by chorea, psychosis and by dementia and usually by premature death. The first signs of the disorder are subtle and difficult to pin down; especially if nothing is known about the family history, as sometimes happens in the case of adoption, for instance. There may be absent mindedness, irritability or depression, accompanied by fidgeting, clumsiness and unexplained falls. Chorea, uncontrolled movements of limbs, trunk or head, develops and increases in intensity. Speech is initially slurred, then becomes incomprehensible and finally stops completely as facial expressions become distorted and grotesque. Cognitive functions deteriorate and eventually dementia ensues, sufferers becoming completely isolated.

The genetic basis for HC has been identified and tests are now available to identify those carriers who will at some time in the future become ill. Much is also known about the neuropathology. In the region of the brain area known as the striatum, specific neurons which employ acetyl choline or gamma-amino-butyric acid (GABA) as their transmitters degenerate. This is followed by widespread loss of neurons in other parts of the brain region known as the basal ganglia where the striatum is found, and also throughout the cerebral cortex.

There are no specific treatments for the disease. Drugs which are used in schizophrenia and which interfere with dopamine receptor action may help to sedate psychiatric patients with HC and also reduce the abnormal movements. Most individuals with HC end up in specialised hospital or nursing units where they stay an average of around seven years before death occurs.

CURRENT DISCOVERY

The quite different abnormal movements which may develop in neurotoptic—treated schizophrenic patients and which go under the general term of tardive dyskinesia (TD) may be helped by treatment with gamma-linolenic acid (GLA) or dihomogammalinolenic acid (DGLA), see for example K S Vaddadi 'Essential Fatty Acids and alpha-Tocopheral Treatment in Tardive Dyskinesia', pp 74–90 in Free Radicals in the Brain; Ageing, Neurological and Mental Disorders, Springer Verlag, Berlin, 1992. Although the movement disorders in TD are quite different from the chorea of HC, I wondered whether GLA might be beneficial and initiated treatment in one of my patients with HC. The woman was Caucasian and 82 years old. She had late onset HC confirmed by genetic analysis and by the family history. She had severe mood swings, severe choreiform movements and impaired speech with early dementia. She had lost a large amount of weight because of the constant movement and difficulty in eating. She was unable to protrude her tongue from her mouth for a sustained period when asked to do so, one of the characteristic features of HC. She was treated with the neuroleptic, haloperidol which blocks dopamine receptors but without any apparent clinical benefit. Various other drugs were tried without any clear effect.

Because nothing seemed to be helping, as a last resort and with no real expectation of benefit I started treating her in her nursing home environment with 160 mg of GLA/day. After eight weeks a completely unexpected degree of improvement had taken place which was obvious to me, to the patient's family and to the nursing home staff. Her abnormal choreiform movements of hands, head and neck, trunk and legs were much reduced and her legs were steady. On request she could protrude her tongue from her mouth for sustained periods. She became much more communicative, took a greater interest in her surroundings and put on several kg in weight because of reduced movements and better eating. Over a period of two years this improvement has been sustained whereas before that, as would be expected from the natural history of the disease, she had been deteriorating rapidly.

I therefore administered a higher dose of GLA, 480 mg/day, to three further patients with Huntington's chorea, two males aged 41 and 58 and one female aged 50. In all, the diagnosis had been conclusively confirmed by genetic testing. I monitored their general clinical changes over nine months and also assessed their motor performance using the well-established Abnormal Involuntary Movements Scale (AIMS). The patients had scores of 19, 25 and 18 on this scale at the start of treatment, which fell to 16, 15 and 10 at the end of nine months. Such improvements are completely unexpected since normally there is inexorable deterioration in Huntington's disease. All of the patients reported subjective improvements in daily living and in memory.

One of the patients was of particular interest. A 58 year old man who had previously been of high intelligence and run his own business had deteriorated steadily over a period of about 15 years. For about seven years he had been unable to tie his own shoelaces or to carry cups of liquid without spilling them. During treatment he improved remarkably and by the end of the nine months was able to tie his shoelaces without assistance and to carry cups of coffee without concern about spilling them.

These case histories demonstrate that the treatment can produce substantial improvement in patients with a disease which has hitherto been thought to be untreatable.

THE INVENTION

I therefore propose that GLA or DGLA may be used to prepare medications for the treatment of HC. Further it is my reasonable expectation, yet to be clinically tested, that if treatment is started early on the basis of genetic testing, prior to the onset of clinical symptoms, then those symptoms may be considerably delayed or even prevented altogether. Thus another aspect of the invention is preparation of medication for the prevention or delay of onset of symptoms in individuals who are clinically normal but who are carriers of the HC gene.

Other members of the essential fatty acid families may optionally be used in addition to GLA or DGLA. Of particular value may be arachidonic acid (AA) and/or docosahexaenoic acid (DHA) which are found in high concentrations in normal neuronal membranes, or the precursors of DHA, stearidonic acid and eicosapentaenoic acid (EPA).

The fatty acids may be provided in doses of from 10 mg to 50g per day, preferably 50 mg to 5g/day and very preferably 100 mg to 2g/day. Any chemical form which leads to a rise in the concentration of GLA, DGLA or one of the other fatty acids in the body fluids may be used in treatment. Particularly useful forms are free fatty acids, salts, glycerides, esters (including cholesterol esters), diesters and phospholipids. Any oral, enteral, parenteral or topical route of administration may be used provided that it delivers adequate levels of the relevant fatty acid into the body fluids. Such levels are essentially of course determined by efficiency, but if the parenteral route is employed there may be problems of haemolysis if the blood plasma concentration is high. High levels can however be monitored, as discussed for example in European Patent Application 93 306 569.0 (0 585 087), at 0.4 to 0.5 millimolar in the first 24–48 hours of a treatment and up to 0.7 millimolar thereafter. Intravenous fatty acids can thus be given indefinitely at such levels if required. However, fatty acids can be given by oral or other convenient routes.

SUMMARY OF INVENTION

The invention may be summarised as follows

1. A method of treating Huntington's Chorea by the administration of effective amounts of GLA or DGLA, and a method of preparation of medications for such purpose using such acids.
2. A method of delaying the onset of Huntington's Chorea or preventing it altogether by administering appropriate amounts of GLA or DGLA to clinically normal individuals who are genetic carriers of the disease, and a method of preparation of medicament for such purpose using such acids.
3. As 1 and 2 but with the addition of AA, DHA, EPA or stearidonic acid or one or more of the other n-6 or n-3 essential fatty acids.

EXAMPLES

The following are examples of compositions to be made by per se conventional methods as medications for the purposes of the invention.

1. A soft or hard gelatin capsule containing 50–500 mg of GLA as evening primrose oil or in any other appropriate form with the recommended dose being 2 to 10 capsules/day.
2. A tablet or pastille containing 100–200 mg of GLA in any appropriate form with the recommended daily dose being 4 to 8 per day.
3. A cream, ointment, whip, foam, pessary, suppository, or emulsion any other appropriate formulation for topical administration containing 0.1 to 10% by weight of GLA.
4. An emulsion or solution for parenteral or enteral or oral administration containing 1% to 30% of GLA by weight.
5. A foodstuff in granule, cream, gel, pastille, flake, powder or any other form known to those skilled in the art containing 0.1 to 10% of GLA by weight.

6–10 As 1–5 but with the active ingredient DGLA.

11–20. As 1–10 but in addition containing 10–300 mg of arachidonic acid, EPA or DHA per unit dose or 0.1% to 10% by weight in formulations for topical, enteral, parenteral or food use.

The following is a particular example of an intravenous infusion fluid, to be used in the manner set out in EPA 0,585,087 as referred to earlier, for the present purposes.

21. Lithium gamma-linolenate or dihomo-gamma-linolenate, with or without eicosapentaenoate, arachidonate, docosahexaenoate, docosapentaenoate (n-3 or n-6), adrenate, linoleate, stearidonate, alpha-linolenate, parinarate, alpha-eleostearate or other essential or related fatty acid lithium salt in addition, is made up at 5–500 mg/ml, preferably 50–200 mg/ml, in an appropriate solution such as 20% ethanol in water or 0.9% saline, in sterile ampoules. Such ampoules are then added to appropriate conventional intravenous fluids such as 0.9% saline, or other appropriate intravenous fluid to achieve a final concentration of 1–100 mg/ml, preferably 5–20 mg/ml in the fluid to be administered. This final intravenous fluid is then slowly administered intravenously to a patient requiring maintenance of hgh plasma fatty acid levels, in order to deliver 1–5,000 mg/kg/day, preferably 50–250 mg/kg/day of the lithium salt to the patient. At, for example, 2 h, 4 h, 6 h, 12 h and 24 h after starting the infusion or at 6, 8, 12, 24 48 or 72 hourly thereafter, blood samples are taken from a vein which is not receiving the infusion, preferably from another limb, and the plasma lithium measured to ensure that it remains within the desired limits of 0.4 or 0.5 millimolar or 0.7 millimolar or higher concentration if desired and if found in the particular patient not to lead to haemolysis.

I claim:

1. A method of treating the symptoms of Huntington's Chorea comprising administering to a patient in need of same an effective amount of gamma-linolenic acid (GLA) or dihomogammalinolenic acid (DGLA).
2. A method of treating the symptoms of Huntington's Chorea comprising administering to a patient in need of same an effective amount of gamma-linolenic acid (GLA) or dihomogammalinolenic acid (DGLA) together with an n-6 or n-3 essential fatty acid.
3. A method of delaying the onset of the symptoms of Huntington's Chorea by administering to a patient in need thereof appropriate amounts of GLA or DGLA to clinically normal individuals who are genetic carriers of the disease.
4. A method of preventing the onset of the symptoms of Huntington's Chorea by administering to a patient in need thereof appropriate amounts of GLA or DGLA to clinically normal individuals who are genetic carriers of the disease.

* * * * *